United States Patent
Lin et al.

(10) Patent No.: US 6,222,902 B1
(45) Date of Patent: Apr. 24, 2001

(54) REAL-TIME TOMOGRAPHIC SYSTEM WITH FLAT PANEL DETECTORS

(75) Inventors: Zhongmin Lin, Twinsburg; Leonard F. Plut, Mentor; Timothy J. Crish, Strongsville, all of OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/200,651

(22) Filed: Nov. 25, 1998

(51) Int. Cl.$^7$ .................................................. G01N 23/00
(52) U.S. Cl. ................................................................ 378/22
(58) Field of Search .......................................... 378/22, 21

(56) References Cited

U.S. PATENT DOCUMENTS

| | | | |
|---|---|---|---|
| 4,139,776 | * | 2/1979 | Hellstrom ................................ 378/22 |
| 4,349,740 | * | 9/1982 | Grassmann et al. ..................... 378/22 |
| 4,853,947 | * | 8/1989 | Haaker et al. ........................... 378/22 |
| 5,978,440 | * | 11/1999 | Kang et al. .............................. 378/22 |

* cited by examiner

Primary Examiner—Craig E. Church
(74) Attorney, Agent, or Firm—Fay, Sharpe, Fagan, Minnich & McKee, LLP (57) ABSTRACT

An object (14) is positioned on an object support (16). A radiation source (10) projects a beam of radiation through a region of interest (12) of the object. A plurality of focal planes ($F_1, F_2, \ldots, F_n$) mark the center of selected slice images through the region of interest. A gantry (20) rotates the radiation source (10) around a circular trajectory (22) as an encoder (26) monitors a radius (r) of the trajectory and an angular position ($\phi$) of the radiation source (10) around the trajectory (22). A look-up table (40) is addressed with the selected focal plane(s) ($F_1, F_2, \ldots, F_n$) and (r, $\phi$) to generate a correction or shift value ($S_1, \ldots, S_n$) for each selected focal plane ($F_1, F_2, \ldots, F_n$). A flat panel detector (18) is read out a plurality of times to generate a plurality of electronic data views as the radiation source rotates. Each view is corrected with a corresponding correction or shift value and integrated in a summation circuit (50) with preceding views to generate an image representation of the slice(s) through the selected focal plane(s) ($F_1, F_2, \ldots, F_n$) or a 3D volume. The slice image or 3D volume image representation is converted into a human-readable display (56) substantially in real-time, e.g., each time a preselected number of views has been summed.

20 Claims, 4 Drawing Sheets

Fig. 5

REAL-TIME TOMOGRAPHIC SYSTEM WITH FLAT PANEL DETECTORS

BACKGROUND OF THE INVENTION

The present invention relates to the diagnostic imaging arts. It finds particular application in conjunction with the real-time display of medical diagnostic images and will be described with particular reference thereto. However, it is to be appreciated that the invention may find application in conjunction with non-medical imaging, volumetric imaging, and the like.

Heretofore, x-rays have been projected through a patient onto a flat film box on the other side of the patient. X-ray film mounted in the film box was exposed with a projection of the radiation opacity of the tissue or other internal structure of an examined subject. Because all of the internal structure was projected into a common plane, such images were difficult to read.

Conventional x-ray tomo systems have a similar construction, but include structure for moving the x-ray tube and the film box counter-cyclically in planes parallel to the x-ray film. More specifically, a center ray of the x-ray beam was projected through the region of interest to the detector. The x-ray source and the detector were then moved such that the central ray pivots about a fixed point in the plane of interest. With this process, not only does the central ray pivot about the plane or slice of interest, the other rays from the x-ray source to the film box do as well. In this manner, the x-ray attenuation contribution to the final image from volumetric elements within the selected plane remains constant during the imaging procedure. However, outside of the selected slice, each of the rays pass through different surrounding tissue or structures as the source and detector move. In this manner, the contributions to the final image from structures outside of the plane of interest become blurred and averaged. With a sufficiently long exposure and motion through a relatively wide range, the out-of-slice structures can be reduced to background noise while the in-slice structures are displayed crisp and clear. Such systems required a significant time lag before the diagnostic image could be viewed. First, there was a delay while the x-ray source and the film box and the film box were moved back and forth to expose the film. This was followed by a further delay as the film was developed.

Real-time images were available from fluoroscopy systems. In a fluoroscopy system, the x-rays are projected through the patient onto an image intensifier, i.e., a fluorescent screen and electronics to make the resultant image brighter. A video camera was mounted to view the image generated by the image intensifier. The video camera was connected by a closed-circuit TV system with a monitor for viewing the fluoroscopic images. Although these images were real-time, they were again projection images which superimposed all the structure in the field-of-view onto a common plane. Moreover, image intensifiers were subject to non-uniform brightness across the field-of-view and significant image distortions. Fluoroscopic images typically had much less resolution than projection x-ray.

CT scanners have been utilized to generate images of internal structures quickly. However, CT scanners typically view the patient in slices which are orthogonal to those of the tomographic x-ray systems. That is, with the patient positioned prone on his back in the scanner, the tomographic x-ray systems generated an image of a horizontal slice. With the same orientation of the patient, CT scanners generate a vertical slice. Of course, CT scanners can be utilized to generate a large multiplicity of slices to define a volume from which a horizontal slice can be extracted. However, taking a large number of slices again introduces a time delay. Moreover, CT scanners are expensive and capable of performing only a limited number of diagnostic tasks.

The present invention contemplates a new and improved imaging technique which overcomes the above-referenced problems and others.

SUMMARY OF THE INVENTION

In accordance with the present invention, an apparatus for real-time diagnostic imaging of an object is provided. A support supports a region of interest of an object to be examined. A radiation source projects a beam of penetrating radiation through the region of interest. A movable gantry causes relative motion between the radiation source and the support. A radiation detector detects the beam of penetrating radiation and converted the detected radiation into electronic data. The radiation detector is repeatedly sampled as the radiation source moves to generate a plurality of electronic views. An image processing circuit processes the plurality of electronic views to generate an electronic image representation of a selected slice through the region of interest, which image representation is continuously updated as the radiation source moves.

In accordance with a more limited aspect of the invention, the moveable gantry rotates the radiation source in an annular trajectory of different radii so that different horizontal slice thicknesses of the object can be monitored in real-time and controlled in real-time by the user.

In accordance with a more limited aspect of the invention, the radius is controlled through a user input device which takes a selected thickness for a region of interest to be depicted in a slice image representation, converts the selected thickness into a corresponding radius value, and adjusts the radiation source to a radius corresponding to the selected radius value.

In accordance with a more limited aspect of the invention, a focal plane selection input device allows an operator to designate a focal plane corresponding to the selected slice, through use of a look-up table, to generate an appropriate section from the plurality of views for display.

A first advantage of the present invention is that it provides a new imaging modality for diagnostic imaging.

Another advantage of the present invention is that it provides a real-time display of slices taken longitudinally through a patient.

Other advantages of the present invention reside in the ready adjustability of the slice thickness and position.

The present system is amenable to imaging in other modes including tomographic, fluoroscopic, and projection x-ray modes.

Other advantages of the present invention reside in the ability to enhance and manipulate images easily.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
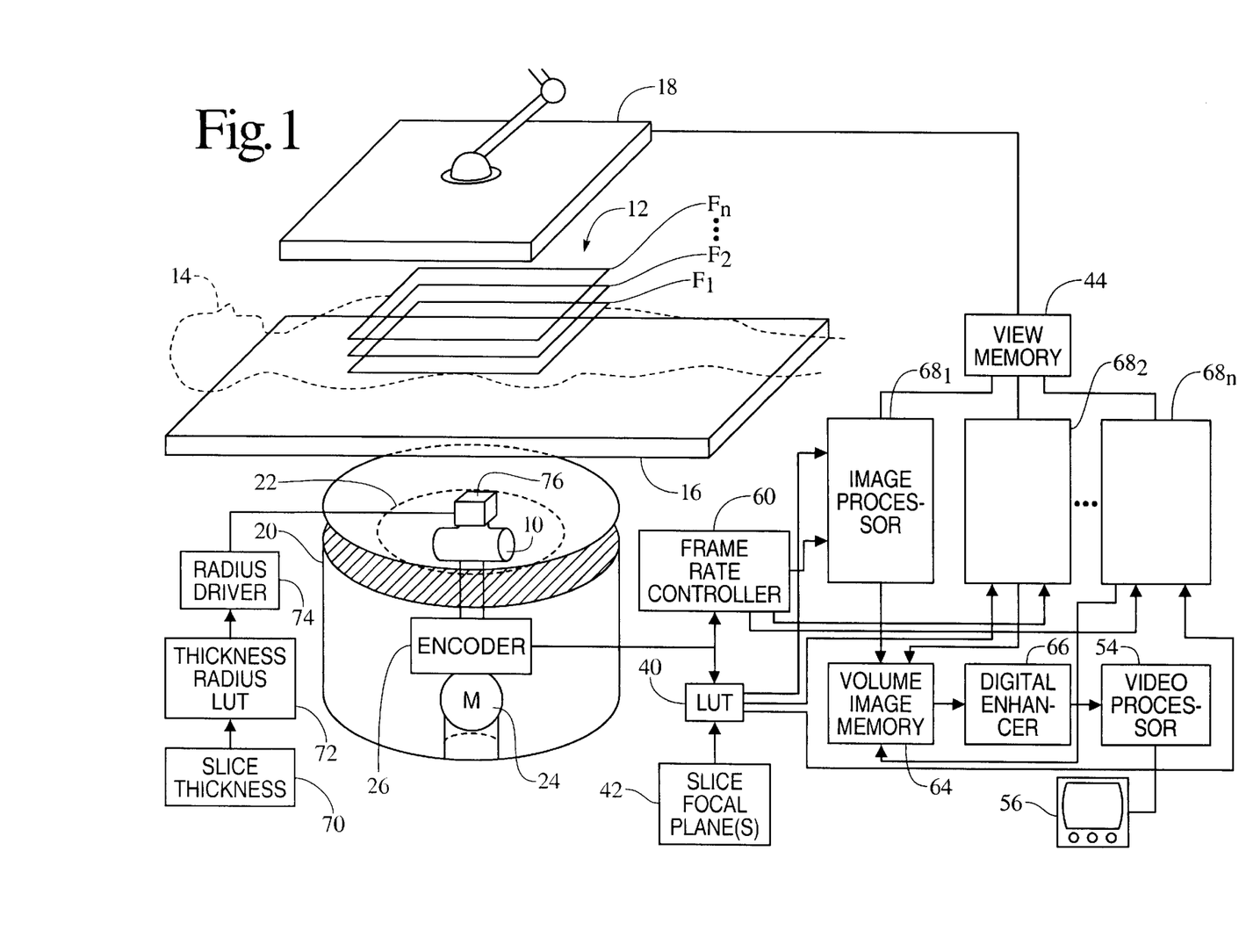
FIG. 1 is a diagrammatic illustration of an imaging system in accordance with the present invention.

With reference to FIG. 1, a radiation source 10, such as an x-ray tube, projects a beam of x-rays or other penetrating radiation through a region of interest 12 of a subject 14, such as a patient or an object in a manufacturing environment, supported on a support 16. Radiation which has passed through the region of interest impinges upon a flat panel radiation detector 18. In the preferred embodiment, the radiation detector is a grid of amorphous silicon elements on the order of a millimeter square, with the overall detector being on the order of 45 cm x 45 cm. Each element of the amorphous silicon detector integrates the intensity of received radiation over a sampling period and generates an electronic data value indicative of the intensity of received radiation. Typically, all of the elements are read out concurrently or in close temporal proximity to generate a view representative of x-ray intensity variation, which, in turn, is indicative of a projection of radiation opacity of the region of interest taken in the direction of the x-ray beam.

The radiation source 10 is mounted on a rotational gantry 20 which rotates the radiation source 10 in an annular, preferably circular, trajectory 22 of adjustable radius. For clarity of illustration, the gantry 20 is illustrated as a concave dish of constant radius relative to a center point of the detector 18. It is to be appreciated that other, more complex mechanical arrangements can be provided for rotating the x-ray source 10 in a circular trajectory 22 of selectable radius along the surface of the dish. For example, the x-ray source 10 can be mounted to a dish segment supported by rollers or bearings with an adjustment drive (not shown) for adjusting the position of the radiation source 10 radially. Once the radius of the circular trajectory 22 is selected, another drive motor 24 rotates the x-ray source 10 around the selected trajectory. A position encoder 26 measures the radius r of the trajectory 22 and the angular position $\phi$ of the x-ray source 10 around the trajectory 22.

Figure 3:
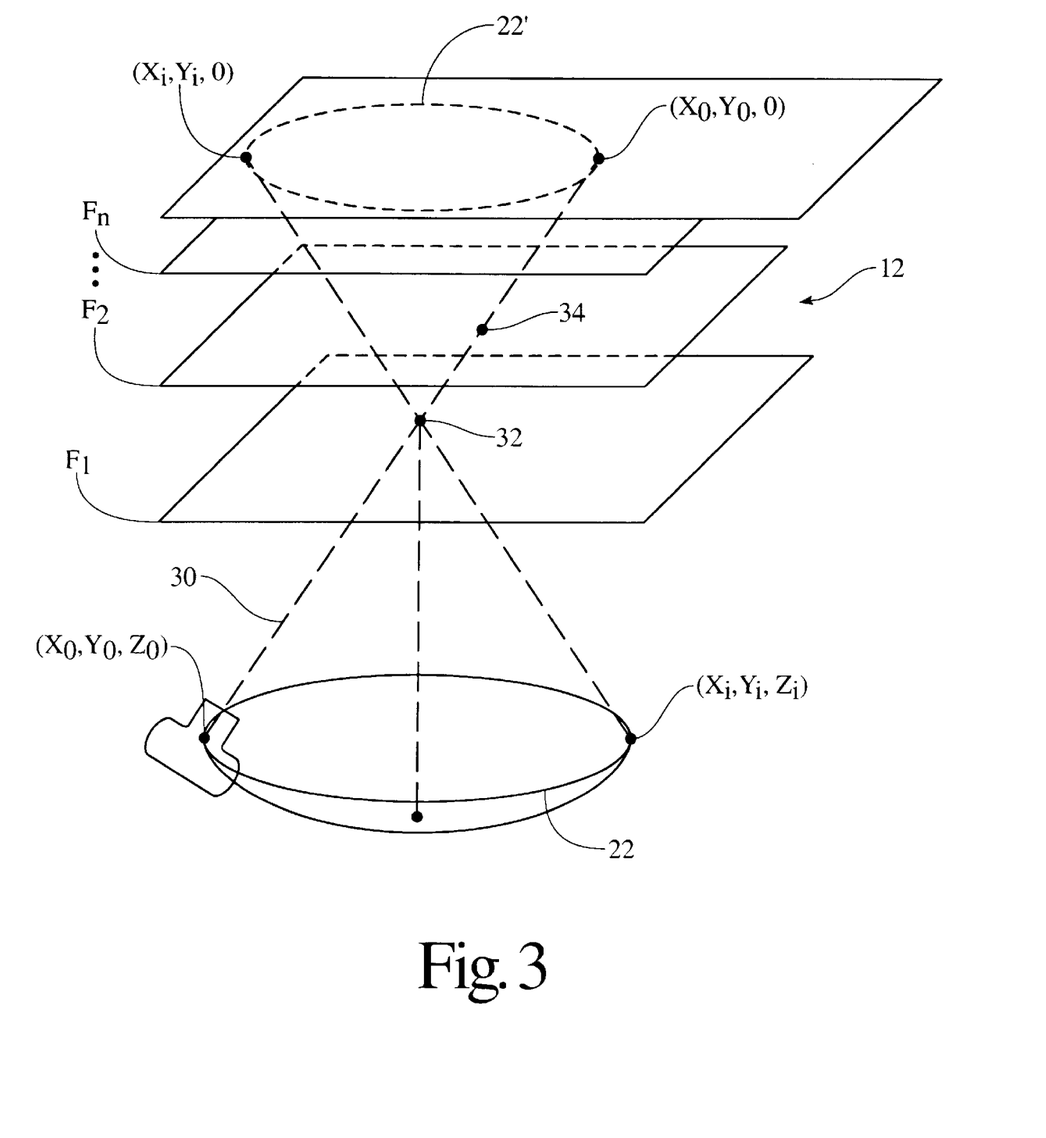
FIG. 3 is a diagrammatic illustration of the geometric principles responsible for structures in the focal plane contributing coherently to the resultant image while structures outside of the focal plane contribute non-coherently and blur.

With reference to FIG. 3, the region of interest 12 is divisible into a series of focal planes $F_1, F_2, \ldots, F_n$. With the x-ray source 10 starting at an arbitrary initial position $(x_0, y_0, z_0)$ on the trajectory 22, the image of incremental element 32 on a first focal plane $F_1$ is located at an initial position $(X_0, Y_0, Z_0)$ on the detector plane, where the z-coordinate of the radiation detector has been arbitrarily selected as $z_0=0$ for simplicity of calculation. As the x-ray source 10 moves around the trajectory 22 to other positions $(X_i, Y_i, Z_0)$, the image of the incremental element 32 now impinges on a point $(x_i, y_i, z_0)$ on the radiation detector 18. In fact, the image of the incremental elements 32 traverses a complementary trajectory 22' on the detector 18.

It will be seen that for any point outside of the focal plane $F_1$, such as a point 34 on focal plane $F_2$, different rays will pass through element 34 and the trajectory of the projection of element 34 onto the detector 18 will follow a different trajectory from trajectory 22'. More specifically, by simple geometry, it can be seen that when the image read out on the detector 18 is translated or shifted such that the point on the trajectory 22' that corresponds to the projection of element 32 are aligned, the images can be enhanced with elements 32 adding coherently. More specifically, all of the points on plane $F_1$ will integrate substantially coherently such that incremental elements of the region of interest lying in plane $F_1$ are integrated coherently and will be strong and clear in the resultant image. On the other hand, the projection of point 34 and other incremental elements of the region of interest that are off the focal plane $F_1$ will sometimes contribute to one pixel of the integrated image and sometimes to others, thus blurring and becoming de-emphasized. With sufficient variation, the out of plane contribution to the image can be reduced to background noise. For any radius r of the circle, and any angular position $\phi$ along the circular trajectory 22, the trajectory 22' can be precalculated. In this manner, for any given position $(r, \phi)$ of the x-ray source around the trajectory 22, the offset $(x_o-x_i, y_o-y_i, z_o-z_i)$ can be determined geometrically and stored. It is further to be appreciated that the same principle holds true for elements on focal plane $F_2$ and the other focal planes through $F_n$.

With reference again to FIG. 1, as the motor 24 rotates the radiation source 10 along the trajectory 22, the encoder 26 monitors the radius r of the trajectory and the angular position $\phi$ of the radiation source 10 around it. The coordinates $(r, \phi)$ are used to address a look-up table 40 which stores the offset or shift $S_i=(x_0-x_i, y_0-y_i, z_o-z_i)$. The look-up table 40 is also addressed with the location of the focal plane to be imaged as input by an operator on a slice or focal plane selection input device 42.

Figure 2:
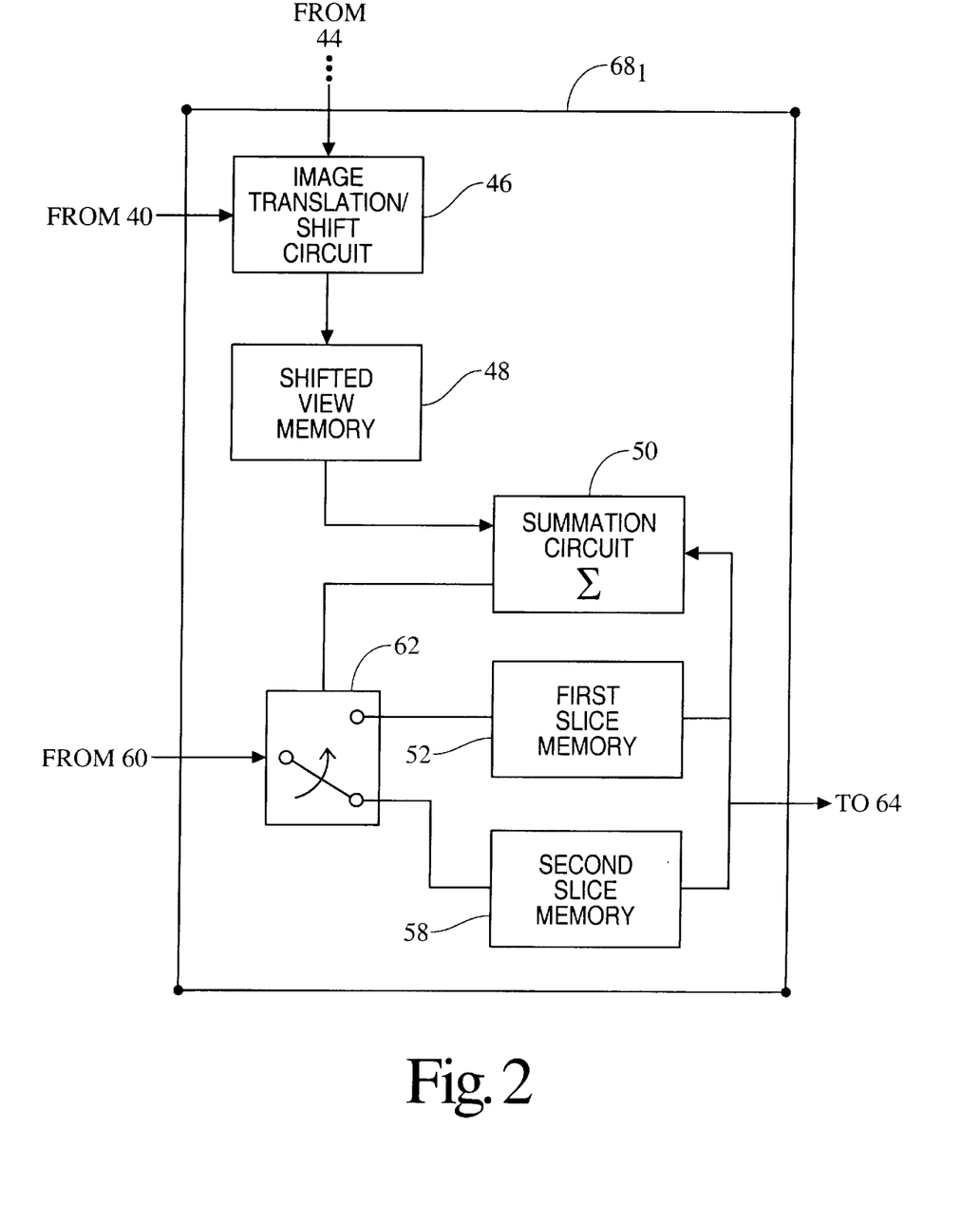
FIG. 2 is a detailed view of an image processor of FIG. 1.

With reference to FIG. 2, and continuing reference to FIG. 1, each time a view is read out of the detector 18, it passes to a view memory or buffer 44. An image translation or shift circuit 46 shifts and interpolates the resultant image by the amount S to create a shifted view which is stored in a shifted view memory or buffer 48. Although buffers 44 and 48 are shown separately for simplicity of illustration, it is to be appreciated that they may be the same element of hardware as may other memories described hereinbelow.

Each shifted image is integrated in summation circuit 50 with precedingly taken images and stored in a first slice memory 52. In the preferred embodiment, the first slice memory 52 is used to accumulate the sum of the views taken over 180° of rotation about the trajectory 22. Once 180° of views are integrated, the first slice memory 52 is interconnected with a video processor 54 which converts the slice image representation from the memory 52 into appropriate format for display on a video monitor 56. While the first slice is being displayed, the x-ray source 10 is rotating through the next 180° and another image is being built in a second slice memory 58. Once the next 180° slice is completed, the second slice 58 memory is connected with the video processor 54 and the first slice memory 52 is erased and commences building the next view of the slice.

Preferably, the x-ray source 10 is rotated at 15 rotations per second such that there is a frame rate of 30 images of the slice generated per second to match a standard video image frame rate. Of course, other frame rates may be selected such as 4–8 images per second. In that case, the x-ray source 10 is rotated at 2–4 rotations per second. Analogously, images may be built based on shorter arc segments such as 120°. As another option, the image may be built in a single memory with the oldest view being subtracted back out as the newest view is added in. As yet another alternative, the views can be continuously accumulated in the slice image memory with no deletions, possibly with the accumulated image and the new view being weighted that more recent views have greater prominence than older views.

The angular position of the x-ray source 10 is monitored by a frame rate controller 60 which changes the position of a switch 62 after each 180° or other selected distance along the trajectory 22. The switch 62 switches which of the memories 52, 58 is connected with the video processor 54 and which is receiving the additional views from the summation circuit 50.

As another alternative, a plurality of planes or slices can be reconstructed. For simultaneous reconstruction of multiple planes, the look-up table 40 is addressed with each of the focal planes selected with the slice selection control 42. The appropriate displacements for each of the focal planes $S_1, S_2, \ldots, S_n$ are outputted to a respective image shifting circuit $46_2, \ldots, 46_n$. The shifted views are conveyed to shifted view memories or buffers $48_2, \ldots, 48_n$. The shifted views are summed $50_2, \ldots, 50_n$ into the accumulating image in buffer $52_2, \ldots, 52_n$ or $58_2, \ldots, 58_n$. The switch circuits $62_2, \ldots, 62_n$ convey the most recently completed slice images to a volumetric image memory 64. The volumetric image memory 64 then conveys the completed slice images through a digital enhancer 66 after the video processor 54 accesses the volumetric image memory 64 to retrieve operator selected slices, an oblique slice, volume renderings, volume images, or the like.

With continuing reference to FIGS. 1 and 2, there are shown a plurality of image processing systems $68_1, 68_2, \ldots, 68_n$. The image processing systems $68_1, 68_2, \ldots, 68_n$ receive inputs from the view memory 44 and Look-Up-Table 40, which are sent to the image transition/shift circuit 46, and they receive inputs the frame rate controller 60 which is sent to the switch 62. The image processing systems $68_1, 68_2, \ldots, 68_n$ then outputs the volume image generated to the volume image memory 64.

Figure 4:
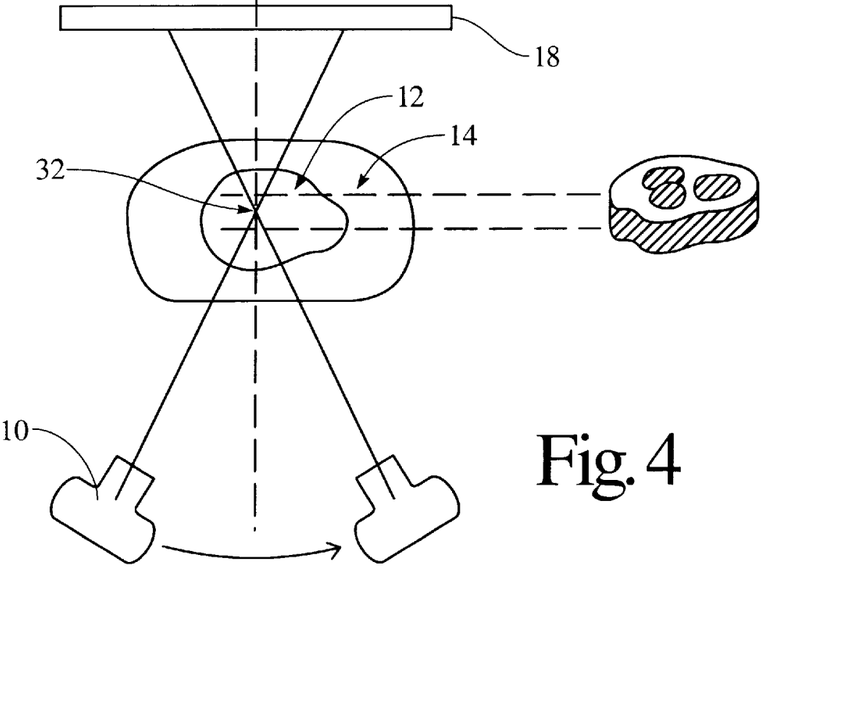
FIG. 4 is a diagrammatic illustration illustrating x-ray tube placement and principles behind generating thin slices; and, FIG. 5 is a diagrammatic illustration illustrating the geometry and principles behind thick slice image generation.
Figure 5:
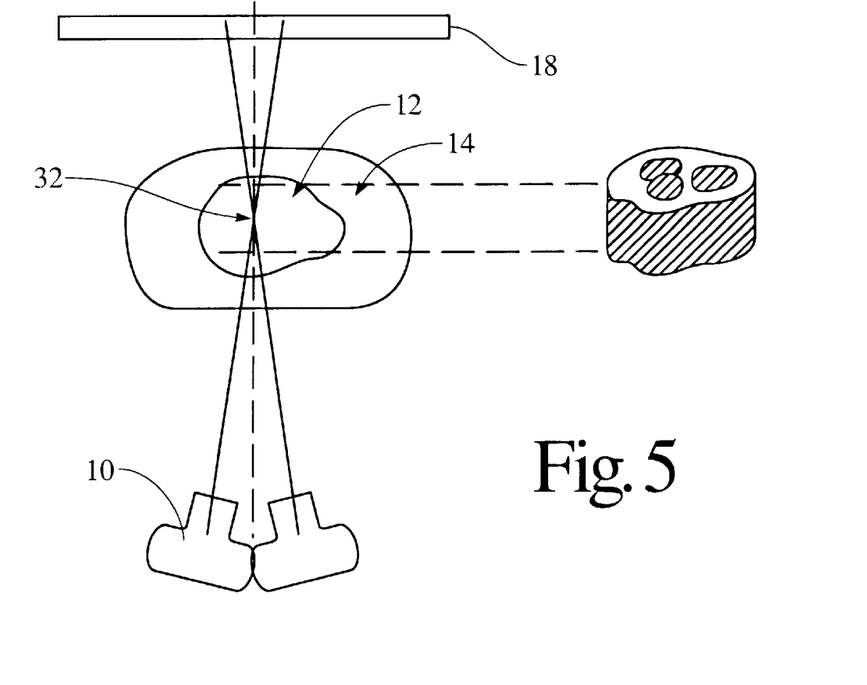

With references to FIGS. 4–5, the operator can select a desired slice thickness with a slice thickness selection input device 70. The selected slice thickness is used as an input into a thickness/radius look-up table 72. Based on the selected slice, the look-up table 72 retrieves the corresponding trajectory radius r. A radius adjustment driver 74 moves the radial position of the radiation source 10 inward or outward in accordance with the selected slice thickness and adjusts the direction of a collimator 76 such that a central ray of the radiation beam is aligned with the center of the detector 18.

As illustrated in FIG. 4, when the radius of the trajectory 22 is relatively large, the radiation beam crosses the point 32 on the selected focal plane at a sharp angle. Due to the sharp angle, incremental elements only a relatively short distance off the focal plane are not held focused with the point 32 as the radiation source moves. In this manner, only data which spans a relatively narrow region to either side of the focal plane remains coherent, hence the resultant image is of a relatively thin slice. As illustrated in FIG. 5, when the radius of the trajectory 22 is very small, the central rays intersect at point 32 at very close angles. When the central ray oscillates about a very narrow range, structures that lie over a more significant distance to either side of the focal plane remain coherently focused on the detector as the radiation source 10 rotates. Hence, the resultant image represents a relatively thick slice. The exact thickness of the slice versus the radius is a relatively straightforward geometric calculation based on the size of the detector elements, the displacement between the detector and the focal plane, the distance between the focal plane and the radiation source, and the radius of the trajectory 22.

Although the radiation source 10 is below the subject 14 in the preferred embodiment, for mechanical simplicity it is contemplated that the radiation source 10 may be disposed above the patient 14 with the detector 18 disposed below or built into the patient support 16.

Although the trajectory 22 is defined along a spherical surface segment, for mathematical simplicity in operating on the resultant data, it is to be appreciated that the trajectories of various sizes could be defined on a flat surface or other surface. Also for mathematical simplicity, each view is subject to the same shift vector S. In some circumstances, it may be advantageous to shift different portions of each view differently. Such differential shifting may reduce edge distortion, may be used to generate oblique plane views, and the like.

It is also to be appreciated that the slice images built in slice image memories 52 and 54 are digital images which can be enhanced using any of a variety of image enhancement techniques. Such techniques include edge enhancement, smoothing, background noise suppression, and the like.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for real-time diagnostic imaging comprising:
   a support for stationarily supporting a region of interest of an object to be examined;
   a radiation source for projecting a beam of penetrating radiation through the region of interest;
   a movable gantry for moving the radiation source with respect to the support;
   a planar radiation detector which spans the region of interest for detecting the beam of penetrating radiation and converting the detected radiation into electronic data, the radiation detector being held stationary and repeatedly sampled as the radiation source moves to generate a plurality of electronic views; and,
   an image processing circuit for processing the plurality of electronic views to generate an electronic image representation of a selected slice or selected volume through the region of interest, which image representation is continuously updated as the radiation source moves.

2. The apparatus as set forth in claim 1 further including:
   an encoder for monitoring a position of the radiation source;
   a second encoder for monitoring a radiation source to image distance;
   an electronic circuit for converting the position of the radiation source monitored by the encoder into a view correction value;
   a circuit for operating on each of the plurality of electronic views in accordance with the view correction value to generate a corrected view for each of the plurality of electronic views;

a view combining device which combines each corrected view with a plurality of the corrected views previously generated to generate the continuously updated image representation.

3. The apparatus as set forth in claim 2 further including:
a first slice image memory and a second slice image memory;
a toggle circuit for connecting the view combining device with a first one of the first and second slice image memories until a preselected number of views have been combined into the image representation, and then zeroing a second one of the first and second slice image memories and connecting the view combining device with the second one of first and second slice image memories until the preselected number of views have been combined into the image representation; and,
a video processor which is connected by the toggle circuit with the one of the first and second slice image memories in which the preselected number of views have been combined for converting the image representation stored therein into appropriate format for display on a monitor.

4. The apparatus for real-time imaging as set forth in claim 3, wherein the encoder monitors the angular position of the radiation source along its annular trajectory, further including:
a frame rate controller which monitors the encoder and changes the position of the toggle circuit after a preselected angular displacement of the radiation source along its annular trajectory; and,
a control circuit which selectably controls a rotational drive motor which rotates the radiation source along its annular trajectory such that said preselected angular displacement corresponds to a frame rate of the video processor.

5. An apparatus for real-time diagnostic imaging comprising:
a support for supporting a region of interest of an object to be examined;
a radiation source for protecting a beam of penetrating radiation through the region of interest;
a moveable gantry which rotates the radiation source in an annular trajectory;
a radiation detector for detecting the beam of penetrating radiation and converting the detected radiation into electronic data, the radiation detector being repeatedly sampled as the radiation source moves to generate a plurality of electronic views;
an image processing circuit for processing the plurality of electronic views to generate an electronic image representation of a selected slice or selected volume through the region of interest, which image representation is continuously updated as the radiation source moves;
a slice thickness selection input device through which an operator selects a slice thickness of structure in the region of interest which contributes to a slice image;
a circuit for converting the slice thickness into a corresponding radius of the annular trajectory; and,
a radius adjusting circuit which controls the gantry to adjust the radius of the annular trajectory.

6. An apparatus for real-time imaging of a plurality of parallel slices comprising:
a support for stationarily supporting a region of interest of an object to be examined;
a radiation source for prolecting a beam of penetrating radiation through the region of interest;
a flat panel radiation detector disposed in a fixed relationship to and spanning the region of interest for detecting the beam of penetrating radiation and converting the detected radiation into a plurality of electronic views;
a movable gantry for moving the radiation source relative to the support and the flat panel detector;
an encoder for monitoring a position of the radiation source;
an electronic circuit for converting the position of the radiation source monitored by the encoder into a view correction value;
a circuit for correcting each of the plurality of electronic views in accordance with (i) the view correction value and (ii) a different shift for each slice through the region of interest to be imaged;
a plurality of view combining circuits each combining the plurality of corrected views corresponding to one of the slices to update concurrently a plurality of slice image representations in real-time; and,
a volume image memory for storing the plurality of slice image representations.

7. The apparatus for real-time imaging as set forth in claim 6, wherein the encoder monitors the angular position of the radiation source along its annular trajectory, further including:
a plurality of pairs of slice image memory, wherein each pair includes a first slice image memory and a second slice image memory;
a plurality of toggle circuits, each toggle circuit connecting (i) one of the plurality of view combining circuits to a corresponding slice image memory pair and (ii) the corresponding slice image memory pair to the volume image memory, wherein each toggle circuit alternately switches (i) the summed image from the corresponding view combining circuit between the first or second slice image memory of the slice image memory pair and (ii) the slice image from the opposing first or second slice image memory of the slice image memory pair to the volume image memory;
a frame rate controller which monitors the encoder and changes the position of each of the plurality of toggle circuits after a preselected angular displacement of the radiation source along its annular trajectory; and,
a frame rate selection circuit which selectably controls a rotational drive motor which rotates the radiation source along its annular trajectory such that said preselected angular displacement is timed to coordinate with a frame rate of a video processor which converts image representations from the volume image memory into appropriate format for display on a monitor.

8. An apparatus for real-time diagnostic imagine comprising:
a support for stationarily supporting a region of interest of an object to be examined;
a radiation source for prolecting a beam of penetrating radiation through the region of interest;
a movable gantry for moving the radiation source relative to the support;
a flat panel radiation detector which spans the region of interest for detecting the beam of penetrating radiation and converting the detected radiation into electronic data, the radiation detector being held stationary and repeatedly sampled as the radiation source moves to generate a plurality of electronic views;

an encoder for monitoring a position of the radiation source;

an electronic circuit for converting the position of the radiation source monitored by the encoder into a view correction value;

a focal plane selection input device through which an operator inputs a designation of a focal plane corresponding to the selected slice, the focal plane selection input device being connected with the electronic circuit for converting monitored position into the view correction value such that the electronic circuit generates appropriate view correction values for the plurality of views for the selected slice;

a circuit for shifting each view correction value such that the electronic circuit shifts each of the plurality of electronic views in accordance with a focal plane of the selected slice, a radius of the trajectory, and an angular position along the trajectory of the radiation source; and, a summation circuit which combines each corrected view with a plurality of the corrected views previously generated to update the image representation with each sampled view.

9. A method of diagnostic imaging comprising:

projecting a beam of radiation through a region of interest of an object with a radiation source;

moving the radiation source relative to the region of interest;

at a stationary monitoring plane which spans the region of interest, converting the beam of radiation which has passed through the region of interest into an electronic view, the beam of radiation being converted into the electronic view a plurality of times during the relative movement the radiation source with respect to the region of interest;

selecting a focal plane through the region of interest to be imaged;

monitoring the relative movement of the radiation source and determining a view correction factor for each view in accordance with a relative position of the radiation source and the selected focal plane through the region of interest to be imaged;

correcting each view in accordance with a corresponding view correction factor;

combining the plurality of corrected views to generate an electronic slice image representation depicting radiation opacity of structures in the slice defined by the selected focal plane;

continuously combining each subsequent corrected view with the slice image representation to update the stored slice image; and, converting the slice image representation to video display format to view the selected focal plane as a continuously updated diagnostic image in real-time.

10. The method as set forth in claim 9 wherein:

the radiation source moves along an annular trajectory which lies in a trajectory plane, which trajectory plane is parallel to the selected focal plane which is parallel to a plane at which radiation is detected and converted into the electronic view.

11. The method as set forth in claim 9, wherein the radiation source moving step includes rotating the radiation source and further including:

coordinating a rate of rotation of the radiation source with a frame rate of the video display format.

12. The method as set forth in claim 9 wherein the relative movement includes rotation of the radiation source around a circular trajectory and further including:

selecting a thickness of the region of interest to be depicted in the slice image representation;

converting the selected thickness into a corresponding selected radius value; and, adjusting a radius of the circular trajectory of the radiation source to a radius corresponding to the selected radius value.

13. The method as set forth in claim 9 wherein:

correcting each generated view includes translating each view; and, combining each generated view includes summing the translated generated views.

14. A method of diagnostic imaging comprising:

a) moving a radiation source relative to a region of interest of an object;

b) projecting a beam of radiation through the region of interest with the radiation source;

c) monitoring the relative position of the radiation source;

d) detecting the radiated beam after it passes through the region of interest at a stationary planar detector which spans the region of interest and generating an electronic view, the detector being sampled a plurality of times during the relative movement of the radiation source with respect to the region of interest to generate a plurality of views;

e) selecting a focal plane through the region of interest to be imaged;

f) determining a view correction factor for each view in accordance with (i) the relative position of the radiation source when the view is sampled and (ii) the selected focal plane through the region of interest to be imaged;

g) correcting each view in accordance with a corresponding view correction factor;

h) combining corrected views with a previously generated slice image representation to generate an updated slice image representation in a first image memory;

i) displaying the updated slice image representation from the first slice image memory on a monitor as subsequently generated corrected views are combined with the updated slice image representation in a second slice image memory to generate a further updated slice image representation;

j) displaying the further slice image representation from the second slice image memory as the further updated slice image representation in the first slice image memory is updated with subsequently generated views; and, k) alternating steps (i) and (j) in accordance with a display rate of the monitor such that the display on the monitor is continuously updated.

15. The method as set forth in claim 14, wherein the step of moving the radiation source includes rotating the radiation source along an annular trajectory and further including:

monitoring angular rotation of the radiation source along the annular trajectory; and, controlling the alternating step (k) to alternate between steps (i) and (j) after a preselected monitored rotation of the radiation source along the annular trajectory.

16. A system for real-time monitoring of a user selected region of interest of an object, the system including:

a radiation source for sending radiation through the user selected region of interest in the object;

a control system for controlling a thickness of a slice through the user selected region of interest during monitoring;

a stationary detector for receiving the radiation passing through the region of interest and generating image data values;

an image processing system which receives the image data values and converts the image data values into display values in real-time to display an image; and, a display device which receives the display values and displays the image for the user while the image processing system concurrently updates the display values with more recently generated image data values.

17. The system as set forth in claim 16, wherein the control system further includes:

a user input device;

a correlation device;

a controller; and, a control device wherein the user inputs a slice thickness value into the user input device which sends the thickness value to the correlation device to determine a corresponding radius value for an annular trajectory of the radiation source, the radius value is then sent to the controller to position the radiation source at the desired radius and to the control device such that the control device controls an angle at which the radiation from the radiation source passes through the region of interest in the object, wherein the angle defines the thickness of the user selected slice being monitored.

18. The system as set forth in claim 17, wherein:

the radiation source is an x-ray source and the detector is a flat panel detector;

the x-ray source is driven around a circular or oval path;

the control device adjusts a radius of the circular or oval light path to allow the flat panel detector to receive the radiation passing through the user selected region of interest of the object, where the thickness of the user selected slice is a thickness within the region of interest of the object which extends horizontally with respect to a focal plane in the object which defines the thickness axis of symmetry; and, the focal plane is parallel with the flat panel detector.

19. The system as set forth in claim 17, wherein:

the thickness of the user selected slice is a plane in the object which is parallel to the detector; and, the control device is controlled by the user during the real-time monitoring of the object to display different thicknesses in real-time correlating to the thickness value input by the user to allow continual adjusting of the thickness during the monitoring.

20. A method of diagnostic imaging comprising:

moving a radiation source relative to a region of interest of an object;

prolecting a beam of radiation through the region of interest with the radiation source;

monitoring the relative position of the radiation source;

detecting the radiated beam after it passes through the region of interest at a stationary flat panel detector which spans the region of interest;

storing the detected image as an electronic view, a plurality of detected images being stored as a corresponding plurality of views during the relative movement of the radiation source with respect to the region of interest;

selecting a plurality of focal planes;

for each focal plane, deriving a corresponding correction factor for each view in accordance with (i) the relative position of the radiation source when the view was detected and (ii) the focal plane;

correcting each view in accordance with the correction factor corresponding to each selected focal plane;

continuously and separately summing the plurality of corrected views for each selected focal plane to generate slice image representations corresponding to each slice;

storing the plurality of slice image representations in a Plurality of pairs of slice image memories, each slice image representation having a corresponding slice image memory pair, each slice image representation being alternately updated with a newly generated view in a first slice image memory as the slice image representation in a second slice image memory of the corresponding slice image memory pair is converted into a frame for display on a monitor; and, alternately switching the first slice image memory and second slice image memory of each slice image pair to display the updated slice image representation and update the image representation again with a yet more recently generated view.

* * * * *